United States Patent [19]

Dorros et al.

[11] 4,429,724
[45] Feb. 7, 1984

[54] PRESSURE GENERATOR FOR INTRAVASCULAR DILATOR

[75] Inventors: Gerald Dorros; Donald A. Spring, both of Milwaukee, Wis.

[73] Assignee: Cardiovascular Diagnostic Services, Inc., Milwaukee, Wis.

[21] Appl. No.: 199,099

[22] Filed: Oct. 20, 1980

[51] Int. Cl.³ .................................. A61M 29/02
[52] U.S. Cl. .............................. 141/27; 141/98; 128/344; 222/390
[58] Field of Search .............. 128/344; 222/390, 336; 141/27, 65, 7, 98, 258, 259, 329, 330; 74/22 R, 22 A, 25, 49

[56] References Cited

U.S. PATENT DOCUMENTS

| | | | |
|---|---|---|---|
| 1,637,189 | 7/1927 | Helberger | 222/336 |
| 2,070,206 | 2/1937 | Hudson | 222/390 X |
| 3,336,925 | 8/1967 | Thompson | 222/390 X |
| 3,756,730 | 9/1973 | Spatz | 222/390 X |
| 3,799,170 | 3/1974 | Walsh et al. | 128/344 |

FOREIGN PATENT DOCUMENTS 573389 6/1924 France ...................... 222/390

*Primary Examiner*—Michael H. Thaler
*Attorney, Agent, or Firm*—Fred Wiviott

[57] ABSTRACT

A pressure generator for intravascular dilators includes a ram and a syringe holder. A screw drive having a large mechanical advantage is coupled for advancing the ram at a controlled rate. A coupler at one end of the ram is adapted to engage one end of a syringe plunger whereby dilation liquid will be discharged at a controlled pressure from the syringe as the ram is advanced. The pressure generator may be provided with a pistol grip and the ram may be calibrated for direct pressure readout.

3 Claims, 2 Drawing Figures

PRESSURE GENERATOR FOR INTRAVASCULAR DILATOR

BACKGROUND OF THE INVENTION

This invention relates to intravascular dilators and more particularly to pressure generators for said dilators.

Intravascular dilators are being employed for a number of medical procedures. For example, some arterial occlusion may be corrected by peripheral dilation catheters. These are tubular catheters having an inflatable section which can be inserted into the affected artery. After proper positioning, the catheter is then pressurized by a dye containing liquid for expanding the inflatable section while appropriate observations are taken. Such procedures require that the pressure within the catheter be closely controlled to permit precise inflation and deflation of the expandable section. Prior art inflation devices were not wholly satisfactory for this purpose because they did not lend themselves readily to precise pressure control and manipulative ease.

SUMMARY OF THE INVENTION

It is a general object of the invention to provide a new and improved pressure generator for peripheral dilation catheters.

A further object of the invention is to provide a pressure generator for peripheral dilation catheters which provides closely controlled pressure adjustments.

Yet another object of the invention is to provide a peripheral dilation catheter pressure generator which may readily be controlled while making visual observations.

DESCRIPTION OF THE PREFERRED EMBODIMENT

Figure 1:
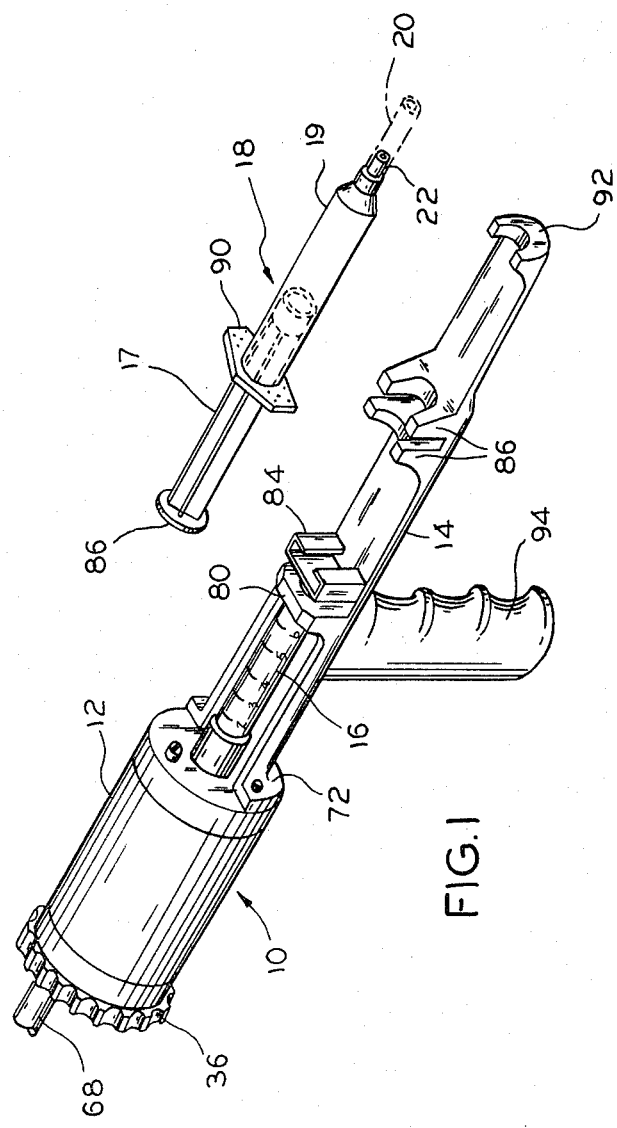

FIG. 1 shows the pressure generator 10 for an intravascular balloon catheter according to the preferred embodiment of the invention to include a drive assembly 12 and a coaxially mounted cradle 14. As will be discussed more fully below, the drive assembly 12 is constructed and arranged to controllably advance and retract a drive rod assembly 16 which is coupled to the plunger 17 of a syringe 18 mounted on cradle 14. In this manner, the fluid within the pressure chamber 19 of syringe 18 will pressurize the interior of pressure tubing 20 connected to a catheter (not shown) coupled to the chamber's discharge end 22.

Figure 2:
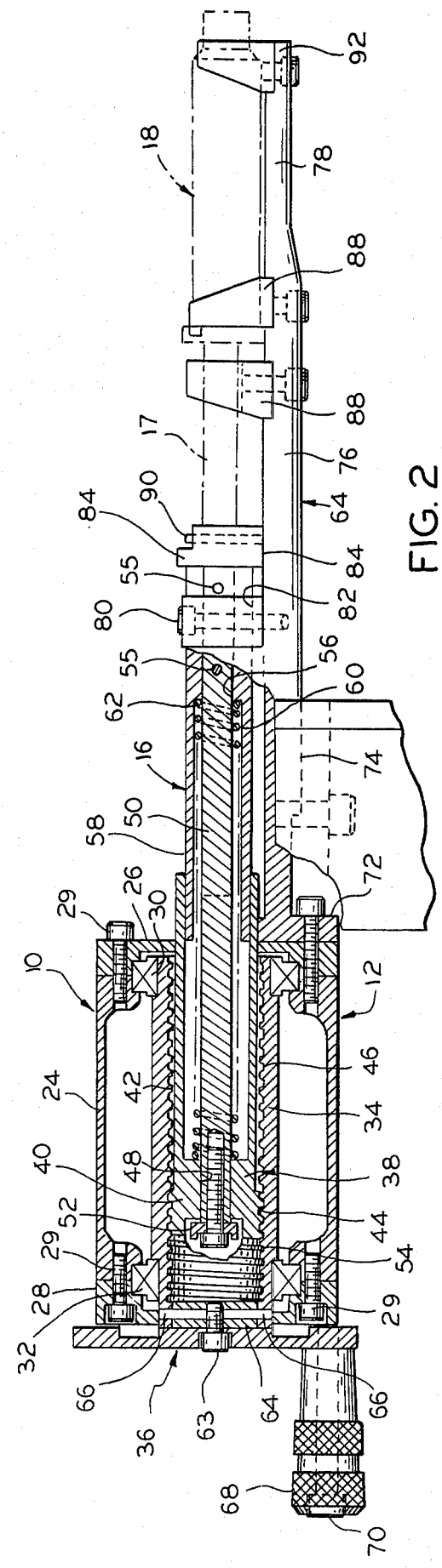

The drive assembly 12 is shown in FIG. 2 to include a hollow, tubular housing 24 having apertured end caps 26 and 28 secured respectively to its opposite ends in any suitable manner such as by screws 29. Mounted between each end of housing 24 and ends caps 26 and 28 are bearing assemblies 30 and 32 for rotatably supporting a hollow tubular barrel 34 is a coaxial relation within housing 24. The barrel 34 is coupled to a hand wheel assembly 36 for being rotated to advance and retract the drive rod assembly 16 which is threadably coupled to the barrel's inner surface. More specifically, the drive rod assembly 16 includes a screw member 38 which has a cylindrical head portion 40 and a coaxial tubular body portion 42. One end of the head portion 40 has external threads 44 for engaging mating threads 46 formed on the interior surface of the barrel 34. The head portion 40 also has a concentric bore 48 for receiving one end of a spring rod 50 which extends coaxially along and out the end of body portion 42. A stop 52 is secured to the proximate end of rod 50 by screw 54 while the opposite end of rod 50 is received within and affixed by means of pins 55 to the cylindrical internal surface 56 formed at one end of a hollow, tubular spring housing 58. The remaining portion of spring housing 58 has a larger diameter inner surface and extends backwardly toward housing 24 for being telescopingly received within the tubular body portion 42 of screw member 38. A spring 60 is disposed in surrounding relation to rod 50 with a first end engaging the head 40 of screw member 38 and its opposite end engaging the transition 62 between surface 56 and the larger internal diameter portion of spring housing 58.

The hand wheel 36 is generally circular and is secured by screws 34 in a coaxial relation to a plug 64 which is disposed within and is coaxial with an unthreaded end of barrel 34. The plug 64 may be secured in barrel 34 in any suitable manner such as by pins 66 which extend through aligned openings in plug 64 in barrel 34. A handle 68 is rotatably mounted by means of a cap screw 70 adjacent the periphery of hand wheel 36 to facilitate rotation.

The cradle 14 is generally elongate and has a flange 72 at one end which is secured to the outer surface of the end cap 26 below the drive rod assembly 16 and in general parallelism therewith. Cradle 14 includes a first semitubular portion 74 extending from flange 72 spaced below the spring housing 62; a second relatively flat intermediate portion 76 and a third portion 78 which is arcuate in cross section for holding the pressure chamber of the syringe 18. Disposed at the transition between the first and second cradle sections is a guide 80 having an aperture 82 for receiving the end of the spring housing 58. Mounted on the end of the spring guide housing 58 and on the remote side of guide 80 is a clamp 84 which is constructed and arranged for receiving the circular end 86 of the syringe plunger 17. In addition, a pair of generally U-shaped stops 86 are disposed in generally parallel spaced apart relation between the sections 76 and 78 for receiving the radial flange 90 which is affixed to the end of the syringe pressure chamber 19. Finally, a generally U-shaped holder 92 is mounted at the end of the section 78 for receiving and supporting the end of the syringe 18. A handgrip 94 may be secured in any suitable manner to the cradle 14 to facilitate holding the assembly during operation. The spring housing guide 80, the stops 87 and the support 92 may be formed integrally on the cradle as shown in FIG. 1 or there may be separate members attached by screws such as shown in FIG. 2.

The operation of the pressure generator 10 will be discussed, for example, with regard to peripheral vascular dilation although it will be appreciated that it may be employed in any procedure requiring a dilation catheter. In this procedure, a three-way stopcock (not shown) is attached between the syringe 18 and the pressure tubing 20. A control syringe (not shown) which may be filled with renograph or conray is attached to the side part of the three-way stopcock. The pressure tubing 20 is then connected to the dilation catheter (not shown) and to the third end of the stopcock. Initially, the peripheral dilation catheter (not shown) is inflated with the control syringe. When the "balloon segment" of the catheter is partially inflated, the handle 70 of the pressure generator 10 is rotated slowly to rotate the barrel 34 to which it is coupled. As the barrel rotates, the screw member 38 will advance toward the right as viewed in FIG. 2 tending to compress the spring 60. The spring in turn urges the spring housing 16 and the rod 50 toward the right and against the end 86 of syringe plunger 17 thereby pressurizing the fluid within the plunger. By selected rotation of handle 78, the pressure within the syringe pressure chamber 19 can be closely controlled. The completion of the dilation can be observed in a fluoroscope and occurs when the expandable section of the catheter "balloons." Upon completion of the procedure, pressure is relieved by turning the handle 36 in the opposite direction.

It will be appreciated that the pitch of threads 44 and 46 determines the advancement of screw member 38 relative to the syringe 18 for each revolution of the hand wheel 36. By thus controlling the rate of advancement of screw member 38, the pressure changes within the syringe 18 and the pressure tubing 20 can be continuously adjusted at a controlled rate.

While only a single embodiment of the invention has been illustrated and described, it is not intended to be limited thereby but only by the scope of the appended claims.

We claim:

1. Pressure generating means for pressurizing a liquid to be delivered at a controlled pressure to a catheter from a container of said liquid, said container including plunger means for expelling and recovering liquid relative to said container, said pressure generator including:

first means adapted to be coupled to said plunger, second means constructed and arranged to be advanced and withdrawn at a controlled rate relative to said first means, said second means including operating means and a first threaded member coupled to said first means and a second threaded member coupled to said operating means, said first means comprising a third member slidably engageable with said first threaded member and being coupled to said plunger means, elongate spring means disposed between said first threaded member and third member for resiliently advancing or retracting said third member relative to said plunger when said first member is rotated, whereby when one of said threaded members is rotated by said operating means in a first direction, said first member and said third member advance toward said container to pressurize the liquid therein, whereby liquid is discharged at a controlled rate from said container to said catheter, and when the one of said threaded members is rotated by said operating means in an opposite direction, said first and third members are displaced away from said container to retract said plunger and withdraw liquid from said catheter and return the same to said container, said first and third members each include hollow tubular portions in telescoping engagement, said spring means being disposed within said tubular portions, and retainer means coupled to said first and third members for preventing the separation thereof, said retainer means including elongate means extending axially through said tubular portions and being engageable at its opposite ends with said first and second members.

2. The pressure generating means set forth in claim 1 and including support means on said housing for supporting said container with said plunger coaxially disposed relative to said tubular members.

3. Pressure generating means for pressurizing a liquid to be delivered and withdrawn at a controlled pressure from a container of said liquid, said container including dispensing means for discharging and recovering pressurized fluid by movement in first and second directions respectively, a catheter connected to said container and having a section expandable to a degree related to the pressure of said liquid, said pressure generating means including:

first means adapted to be coupled to said dispensing means, threaded means including a first portion coupled to said first means and a first threaded member, said first means comprising a second member slidably engageable with said first threaded member, said second member being coupled to said dispensing means, said first threaded member being constructed and arranged to be advanced and withdrawn at a controlled rate relative to said second member whereby the advancement of said second member will move said dispensing means in its first direction to discharge the fluid from the container at a controlled pressure to said catheter and withdrawal of said first threaded member will move said dispensing means in its second direction for recovering said fluid from said catheter, recovery of said fluid, and retainer means including elongate means extending axially through said tubular portions and engageable at its opposite ends with said first and second members for preventing the separation thereof.

* * * * *